United States Patent [19]
Iida et al.

[11] Patent Number: 6,007,480
[45] Date of Patent: Dec. 28, 1999

[54] REDUCED NOISE ELECTRIC ENDOSCOPE SYSTEM

[75] Inventors: Mitsuru Iida; Katsuhiko Furuya; Takayuki Enomoto, all of Tokyo, Japan

[73] Assignee: Asahi Kogaku Kogyo Kabushiki Kaisha, Tokyo, Japan

[21] Appl. No.: 08/912,345

[22] Filed: Aug. 18, 1997

[30] Foreign Application Priority Data

Aug. 19, 1996 [JP] Japan .................................. 8-217100

[51] Int. Cl.⁶ .................................................. A61B 1/05
[52] U.S. Cl. ............................................ 600/109; 348/76
[58] Field of Search ................................ 600/109, 110; 348/65, 75, 76

[56] References Cited

U.S. PATENT DOCUMENTS

| | | |
|---|---|---|
| 4,860,095 | 8/1989 | Kimura et al. .............................. 358/98 |
| 5,543,831 | 8/1996 | Tsuji et al. . |
| 5,569,158 | 10/1996 | Suzuki et al. ............................ 600/110 |
| 5,702,345 | 12/1997 | Wood et al. ............................. 600/132 |

*Primary Examiner*—John P. Leubecker
*Attorney, Agent, or Firm*—Greenblum & Bernstein, P.L.C.

[57] ABSTRACT

An electronic endoscope system includes an electronic endoscope, and a video processor. The video processor transmits a clock signal to the electronic endoscope in order to generate a driving signal for driving a CCD provided therein. The clock signal transmitted from the video processor has a sinusoidal waveform, and the electronic endoscope has a circuit which generates the driving signal based on the clock signal transmitted from the video processor. The driving signal is a periodical signal having a rectangular waveform. Further, a signal transmission line, which transmits the driving signal from the circuit to the CCD, is inserted into and wound around a ferrite material.

6 Claims, 2 Drawing Sheets

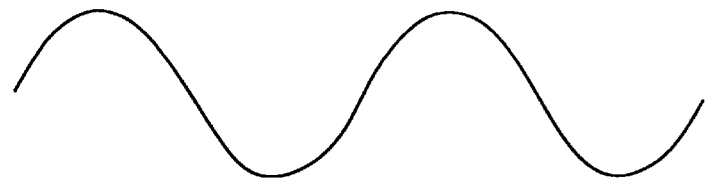
FIG. 2(A)
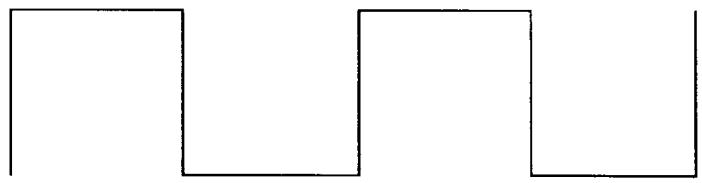
FIG. 2(B)
FIG. 3
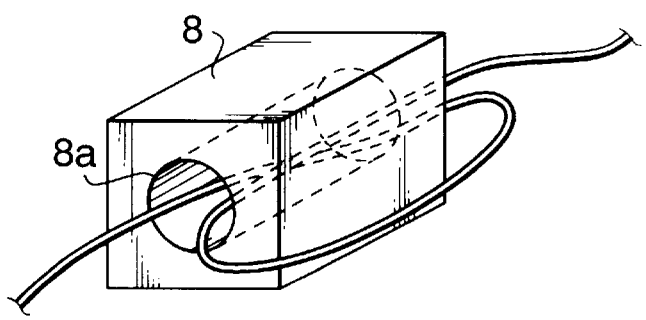

6,007,480

REDUCED NOISE ELECTRIC ENDOSCOPE SYSTEM

BACKGROUND OF THE INVENTION

The present invention relates to an electronic endoscope system including an electronic endoscope and a video processor connected to the electronic endoscope.

Conventionally, the electronic endoscope includes a solid-state image pickup device, such as a CCD (Charge Coupled Device), to capture an image of an affected part or the like. The electronic endoscope further includes a driving circuit for driving the solid-state image pickup device. Since the driving circuit must be substantially matched with characteristics of the solid-state image pickup device, each electronic endoscope includes a driving circuit that is adjusted for the image pickup device provided in that electronic endoscope.

The video processor which is connected with the electronic endoscope sends clock pulses required for generating driving signals in the driving circuit of the electronic endoscope. However, the clock pulses must have a relatively high frequency (e.g., 8 MHz) which may constitute a noise source. The noise generated may not be reduced by grounding because, in order to protect a patient, circuits in a medical instrument, such as the electronic endoscope system, cannot be grounded.

When noise is produced, the noise forms a capacitive coupling with ground or with ungrounded metal components, and the like, and the noise may radiate outside of the electronic endoscope or out of a cable connecting the electronic endoscope with peripheral equipment. In such a case, the cable may function as an antenna, producing an adverse influence on images displayed using the electronic endoscope system itself, and/or cause malfunctions.

SUMMARY OF THE INVENTION

It is therefore an object of the present invention to provide an electronic endoscope system with reduced noise radiation. The reduced noise radiation is allowed by an electronic endoscope functioning as an antenna to radiate, penetrate and appear on displayed images.

According to an aspect of the present invention, there is provided, an electronic endoscope system including an endoscope unit and a video processor. The endoscope unit includes a connector section and an electronic endoscope. The electronic endoscope is provided with a solid-state image capturing device for capturing endoscopic images, and the connector section. The connector section is provided with a driving circuit for transmitting a drive signal to the solid-state image capturing device. The video processor outputs a clock pulse signal. An image signal is transmitted from the solid-state image capturing device to the video processor via the connector section. In particular, the clock pulse signal, which has a sinusoidal waveform, is transmitted to the driving circuit, and the driving circuit generates a periodic rectangular waveform drive signal based on the clock pulse signal.

In a particular case, the driving signal is transmitted from the driving circuit to the solid-state image capturing device through a driving signal transmission line. In this case, the driving signal transmission line is preferably passed through a ferrite member between the driving circuit and the solid-state image capturing device, in the vicinity of the driving circuit.

Further, in this particular case, a command signal transmission line, for sending control commands from the electronic endoscope to the video processor, may be inserted through a ferrite member provided in the electronic endoscope. More particularly, the driving signal transmission line and the control signal transmission line may be inserted through the same ferrite member.

Still further, at least one of the driving signal transmission line and the control signal transmission line may be passed through and wound around the ferrite member a plurality of times.

DESCRIPTION OF THE ACCOMPANYING DRAWINGS

FIG. 1 is a schematic block diagram of an overall configuration of an electronic endoscope system according to an embodiment of the present invention;

FIGS. 2(A) and 2(B) are graphs illustrating clock pulse signal waveforms; and

FIG. 3 is a perspective view of a ferrite member used in the electronic endoscope system of FIG. 1.

DESCRIPTION OF THE EMBODIMENT

Figure 1:
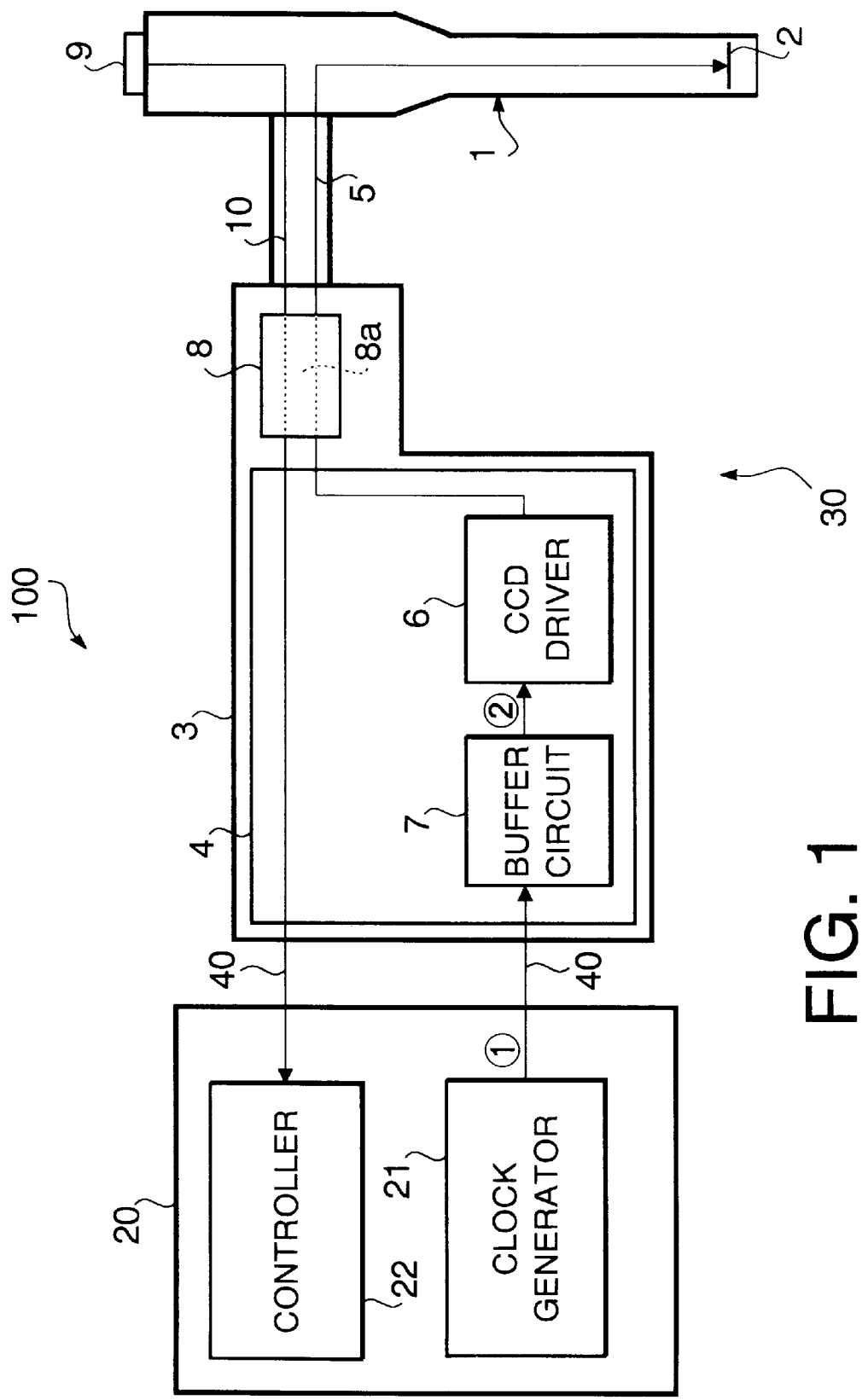

An electronic endoscope system according to an embodiment of the present invention will be described with reference to the accompanying drawings.

FIG. 1 shows an electronic endoscope system 100, which includes a video processor 20 and an electronic endoscope unit 30. The electronic endoscope unit 30 includes an electronic endoscope 1 and a signal connector 3.

The electronic endoscope 1 has a solid-state image pickup device, such as a CCD (charge coupled device) 2, which is provided at a tip of an insert section of the endoscope 1 for capturing endoscopic images.

The signal connector 3 of the electronic endoscope 1 is detachably connected to the video processor 20 through cables 40.

The video processor 20 includes a controller 22, a clock generator 21, and various other circuits (not shown) including, for example, a processing circuit (not shown) for processing video signals picked up by the CCD 2.

In the signal connector 3, a CCD driving circuit 6 is provided on a circuit board 4. The CCD driving circuit 6 outputs driving signals for driving the CCD 2 through a driving signal transmission line 5, composed of a coaxial cable, to the CCD 2. Although not shown, various other circuits are also arranged on the circuit board 4.

In order for the CCD driving circuit 6 to generate the driving signals, a clock pulse signal is required. In the electronic endoscope system 100 according to the embodiment, the clock pulse signal is generated by the clock generator 21 in the video processor 20, and is transmitted through the cables 40 and a buffer circuit 7 to the CCD driving circuit 6. The buffer circuit 7 is, for example, a standard logic integrated circuit, number LS241, LS244, LS365, or the like.

In the embodiment, the clock pulse signal output from the clock generator 21 has a rounded, sinusoidal waveform such as that shown as an example in FIG. 2(A). By using the clock pulse signal having a sinusoidal waveform between the video processor 20 and the endoscope unit 30, radiation of noise through the cables 40 is suppressed.

However, the sinusoidal waveform clock pulse signal cannot be used to drive the CCD 2. Therefore, the clock pulse signal which is input from the video processor 20 is converted into a rectangular waveform clock signal, as shown in FIG. 2(B), by a waveform shaping circuit included in the buffer circuit 7. The converted clock signal is then transferred from the CCD driving circuit 6 to the CCD 2.

Because the driving signal sent from the CCD driving circuit 6 to the CCD 2 has a rectangular waveform and a high frequency, the driving signal tends to produce noise. In order to decrease the amount of noise produced, the signal transmission line 5, through which the driving signal flows, is passed through a ferrite member 8 (or, ferrite core) in the vicinity of the circuit board 4 on which the CCD driving circuit 6 is arranged.

As shown in FIG. 1, the ferrite member 8 has a hole 8a formed therein, and the signal transmission line 5 passes through the hole 8a. FIG. 3 illustrates an alternative arrangement in which the signal transmission line 5 passes through the hole 8a of the ferrite member 8, is wound around the ferrite member 8, and passes through the hole 8a again. Further, in a similar way, the signal transmission line 5 may be wound around the ferrite member 8 a plurality of times, passing through the hole 8a each time. The use of the ferrite member 8 is more particularly disclosed in U.S. Pat. No. 5,543,831, the teachings of which are incorporated herein by reference.

Referring to FIG. 1 again, the controller 22 is disposed in the video processor 20 and is connected with control buttons 9 for inputting control items to the controller 22. The control button disposed at a manipulation section of the electronic endoscope 1. Control signals, generated by manipulating the control button 9, are sent to the controller 22 through a control signal transmission line 10 which is composed of, for example, shielded wires.

Similar to the drive signal transmission line 5, the control signal transmission line 10 also passes through the ferrite member 8 in the electronic endoscope 1. The control signal transmission line 10 may pass through another ferrite member 8 or the same ferrite member 8 if it does not produce an adverse influence.

By inserting the control signal transmission line 10 through the ferrite member 8 as described above, it is possible to reduce noise which is radiated from the control signal transmission line 10, and/or induced in the control signal transmission line 10.

In the electronic endoscope system according to the embodiment of the present invention, radiation of noise is reduced because the endoscope system is configured such that the video processor sends a clock pulse signal having a sinusoidal waveform, and the rectangular clock signal is generated only generated inside the endoscope unit. Further, in the electronic endoscope system according to the embodiment, radiation and penetration of noise is further reduced after the clock signal is converted into a signal having a rectangular waveform, by using the ferrite member. Accordingly, the electronic endoscope system produces less noise, as a whole, and therefore, noise on images displayed on the electronic endoscope system itself is also reduced.

The present disclosure relates to subject matter contained in Japanese Patent Application No. HEI 08-217100, filed on Aug. 19, 1996, which is expressly incorporated herein by reference in its entirety.

What is claimed is:

1. An electronic endoscope system, comprising:

an endoscope unit including a connector section and an electronic endoscope, said electronic endoscope provided with a solid-state image capturing device for capturing endoscopic images, said connector section provided with a driving circuit for transmitting a drive signal to said solid-state image capturing device and a waveform shaping circuit; and a video processor which outputs a clock pulse signal;

wherein an image signal is transmitted from said solid-state image capturing device to said video processor via said connector section;

wherein said clock pulse signal has a sinusoidal waveform and is transmitted to said driving circuit: and wherein said driving circuit generates said drive signal based on said clock pulse signal, and said drive signal is a periodic signal having a rectangular waveform, such that the waveform shaping circuit to converts said sinusoidal wave into a rectangular wave at the endoscope unit.

2. The electronic endoscope system according to claim 1, wherein said driving signal is transmitted from said driving circuit to said solid-state image capturing device through a driving signal transmission line, and wherein said driving signal transmission line is passed through a ferrite member between said driving circuit and said solid-state image capturing device, in the vicinity of said driving circuit.

3. An electronic endoscope system according to claim 2, wherein a command signal transmission line for sending control commands from said electronic endoscope to said video processor is inserted through a ferrite member provided in said electronic endoscope.

4. An electronic endoscope system according to claim 3 wherein said driving signal transmission line and said control signal transmission line are inserted through the same ferrite member.

5. An electronic endoscope system according to claim 3, wherein at least one of said driving signal transmission line and said command signal transmission line are passed through and wound around said ferrite member a plurality of times.

6. The electronic endoscope according to claim 1, further comprising a cable connecting the video processor to the endoscope unit, the sinusoidal wave form being transmitted through the cable.

* * * * *